(12) United States Patent
Modi

(10) Patent No.: US 6,350,458 B1
(45) Date of Patent: *Feb. 26, 2002

(54) MIXED MICELLAR DRUG DELIVER SYSTEM AND METHOD OF PREPARATION

(75) Inventor: Pankaj Modi, Ancaster (CA)

(73) Assignee: Generex Pharmaceuticals Incorporated, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/543,988

(22) Filed: Apr. 6, 2000

Related U.S. Application Data

(63) Continuation-in-part of application No. 09/386,285, filed on Aug. 31, 1999, which is a continuation-in-part of application No. 09/216,733, filed on Dec. 21, 1998, which is a continuation-in-part of application No. 09/021,114, filed on Feb. 10, 1998, now Pat. No. 6,017,545.

(51) Int. Cl.⁷ ........................... A61K 9/00; A61K 9/127; A61K 38/28; A61F 13/00; A01N 37/18

(52) U.S. Cl. .................. 424/400; 424/450; 424/422; 424/434; 514/2; 514/3

(58) Field of Search ................... 424/450, 400, 424/422, 434; 514/2, 3

(56) References Cited

U.S. PATENT DOCUMENTS

| | | |
|---|---|---|
| 4,156,719 A | 5/1979 | Sezaki et al. |
| 4,579,730 A | 4/1986 | Kidron et al. |
| 4,614,730 A | 9/1986 | Hansen et al. |
| 5,053,389 A | 10/1991 | Balschmidt et al. |
| 5,230,884 A | 7/1993 | Evans et al. |
| 5,292,499 A | 3/1994 | Evans et al. |
| 5,376,646 A | 12/1994 | Pittrof et al. |
| 5,629,011 A | 5/1997 | Illum |
| 5,653,987 A | 8/1997 | Modi et al. |
| 5,656,277 A | 8/1997 | Berlati et al. |
| 5,676,931 A | 10/1997 | Adjei et al. |
| 5,747,066 A | 5/1998 | Pittrof et al. |
| 6,017,545 A | 1/2000 | Modi |

*Primary Examiner*—Thurman K. Page
*Assistant Examiner*—Todd D Ware
(74) *Attorney, Agent, or Firm*—Debra Z. Anderson; Eckert Seamans Cherin & Mellott, LLC

(57) ABSTRACT

Pharmaceutical compositions comprising a macromolecular pharmaceutical agent in micellar form are disclosed. The micelles are formed from an alkali metal alkyl sulfate, and at least one additional micelle-forming compound as described in the specification. An alkali metal salicylate and a pharmaceutically acceptable edetate are also included in the composition. Micelle size ranges between about 1 and 10 nanometers. Methods for making and using the compositions are also disclosed.

31 Claims, No Drawings

MIXED MICELLAR DRUG DELIVER SYSTEM AND METHOD OF PREPARATION

CROSS REFERENCE TO RELATED APPLICATIONS

This Application is a continuation-in-part of application Ser. No. 09/386,285 filed Aug. 31, 1999, which was a continuation-in-part of application Ser. No.09/216,733, filed Dec. 21, 1998, which was a continuation-in-part of application Ser. No. 09/021,114, filed Feb. 10, 1998 now U.S. Pat. No. 6,017,545.

FIELD OF THE INVENTION

The present invention relates to an improved pharmaceutical composition comprising macromolecule pharmaceuticals in micellar form. The pharmaceutical compositions are particularly effective in oral, nasal and buccal applications. The present invention further relates to methods for preparing and using these pharmaceutical compositions. Methods for enhancing the rate of absorption of a macromolecular pharmaceutical agent are also disclosed.

BACKGROUND INFORMATION

Relatively little progress has been made in reaching the target of safe and effective oral formulations for macromolecules, including peptides and proteins. Barriers to developing oral formulations for proteins and peptides include poor intrinsic permeability, lumenal and cellular enzymatic degradation, rapid clearance, and chemical instability in the gastrointestinal (GI) tract. Pharmaceutical approaches to address these barriers that have been successful with traditional small, organic drug molecules have not readily translated into effective peptide and protein formulations.

Various routes of administration other than injection for proteins and peptides have been explored. Oral and nasal cavities have been of particular interest. The ability of molecules to permeate the oral mucosae appears to be related to molecular size, lipid solubility and peptide protein ionization. Molecules less than 1000 daltons appear to cross oral mucosae rapidly. As molecular size increases, the permeability of the molecule decreases rapidly. Lipid soluble compounds are more permeable than non-lipid soluble molecules. Maximum absorption occurs when molecules are un-ionized or neutral in electrical charges. Charged molecules, therefore, present the biggest challenges to absorption through the oral mucosae.

Most proteinic drug molecules are extremely large molecules with molecular weights exceeding 6000 daltons. In addition to being large, these molecules typically have very poor lipid solubility, and are often practically impermeable. Substances that facilitate the absorption or transport of large molecules (>1000 daltons) across biological membranes are referred to in the art as "enhancers" or "absorption aids." These compounds include chelators, bile salts, fatty acids, synthetic hydrophilic and hydrophobic compounds, and biodegradable polymeric compounds. Many enhancers lack a satisfactory safety profile respecting irritation, lowering of the barrier function, and impairment of the mucocilliary clearance protective mechanism.

Some enhancers, especially those related to bile salts, and some protein solubilizing agents give an extremely bitter and unpleasant taste. This makes their use almost impossible for human consumption on a daily basis. Several approaches have been utilized to improve the taste of the bile salt-based delivery systems, including patches for buccal mucosa, bilayer tablets, controlled release tablets, use of protease inhibitors and various polymer matrices. These technologies fail to deliver proteinic drugs in the required therapeutic concentrations. Further, film patch devices result in severe tissue damage in the mouth. Other attempts to deliver large molecules via the oral, nasal, rectal, and vaginal routes using single bile acids or enhancing agents in combination with protease inhibitors and biodegradable polymeric materials similarly failed to achieve therapeutic levels of proteinic drugs in the patient. Single enhancing agents fail to loosen tight cellular junctions in the oral, nasal, rectal and vaginal cavities for the time needed to permit passage of large molecules through the mucosal membranes without further degradation. These problems make it impractical to use many systems.

U.S. Pat. No. 5,690,954 discloses a drug delivery system utilizing bioadhesive microspheres each having an active drug and an absorption-enhancing material. The patent does not appear to teach micelles of the size or nature of those disclosed in the present invention.

U.S. Pat. No. 5,053,389 claims a method for treating diabetes in a warm-blooded animal by nonparentaral administration of an insulin preparation comprising des[(B26-30)-pentapeptide] insulin-B25-amide, an absorption promoting substance, a physiologically acceptable additive and, optionally, a conventional insulin. The absorption-promoting substance and physiologically acceptable additive can be bile acids and glycerine, respectively.

U.S. Pat. No. 4,614,730 discloses processes for preparing insulin solutions stabilized by the presence of one or more phospholipids, preferably a lecithin; the solutions can also contain a zinc salt, a preservative, an isotonic agent and/or a buffering agent.

U.S. Pat. No. 5,230,884 discloses an aerosol formulation for delivery of insulin to a patient's lungs comprising a propellant, insulin, and a surfactant which is present as reverse micelles dispersed in the propellant; the insulin is solubilized in the reverse micelles. The pH of the aqueous fluid associated with the surfactant is less than 5.5. Methods for preparing these aerosol formulations are also disclosed in the '884 patent as well as U.S. Pat. No. 5,292,499.

U.S. Pat. No. 5,376,646 relates to a method for facilitating penetration and distribution of a pharmaceutically active substance into the skin, which preparation includes the pharmaceutically active substance, a salt of cholanic acid, and phosphatidyl choline in an effective amount to facilitate penetration and distribution of the substance into the skin. The salt of a cholanic acid can be sodium glycocholate, and the phosphatidyl choline is lecithin.

U.S. Pat. No. 5,663,198 discloses a drug formulation with a fluorinated hydrocarbon and micronized particles of a sparingly water-soluble drug that are coated with a physiologically acceptable ampholytic phospholipid surfactant to give a micellar/colloidal solution. The phospholipid disclosed is a phosphatidylcholine.

U.S. Pat. No. 5,506,203 discloses a method of treating a patient in need of insulin treatment by introducing into the lower respiratory tract a dry powder formulation comprising insulin and an absorption enhancer. Absorption enhancers disclosed include salts of fatty acids such as sodium laurate, bile salts and bile salt derivatives such as glycocholate, and phospholipids such as lysophosphatidylcholine. Other potentially useful surfactants disclosed include sodium salicylate. One chelator tested was EDTA, which was found to be ineffective as an absorption enhancer in rat models.

U.S. Pat. No. 5,424,289 relates to an orally administerable enteric coated capsule containing an effective amount of a peptide, sodium salicylate, and an oil. Oils disclosed include peanut oil, mineral oil, silicone oil, coconut oil, corn oil, sesame oil, olive oil, fatty acids, vitamin E and the like. Preferred oils are peanut oil and corn oil.

Powdered formulation for pulmonary administration of insulin, and methods for making and using the same are disclosed in U.S. Pat. Nos. 5,898,028; 5,747,445; 5,658,878; and 5,952,008.

U.S. Pat. No. 5,653,987 discloses a liquid pharmaceutical agent suitable for oral or nasal delivery comprising a proteinic pharmaceutical agent, water and at least two absorption enhancing compounds. The '987 patent does not teach the use of the particular absorption enhancing compounds in the manner of the present invention.

Accordingly, there remains a need for improved therapeutic formulations, particularly those comprising macromolecules and particularly those useful for oral and nasal application.

SUMMARY OF THE INVENTION

The present invention addresses the above need by providing an improved pharmaceutical composition comprising a macromolecular pharmaceutical agent, an alkali metal alkyl sulfate, a pharmaceutically acceptable edetate, an alkali metal salicylate and at least one additional micelle-forming compound, in a suitable solvent. The agent can be one or more proteins, peptides, hormones, vaccines or drugs. The molecular weight of the macromolecular pharmaceutical agent preferably ranges between about 1,000 and 2,000,000 daltons. The agent is presented in micellar form, with a micelle size of approximately one to 10 nanometers (nm).

As used herein the term "mixed micelles" refers to at least two different types of micelles, each of which has been formed using different micelle forming compounds; for example, the present compositions comprise a mix of at least two different types of micelles—micelles formed between the pharmaceutical agent and alkali metal alkyl sulfate, and micelles formed between the pharmaceutical agent and at least one different additional micelle forming compound as disclosed herein. It will be understood that each individual micelle can be formed from more than one micelle forming compound as well. The mixed micelles of the present invention tend to be smaller than the pores of the membranes in the oral cavity or the GI tract. It is therefore believed that the extremely small size of the present mixed micelles helps the encapsulated macromolecules penetrate efficiently through the oral mucosa. Thus, the present compositions offer increased bioavailability of active drug, particularly across oral mucosa, when compared with pharmaceutical preparations known in the art.

The present invention is also directed to a method for enhancing the rate of absorption of a macromolecular pharmaceutical agent comprising administering a composition comprising the agent in combination with an alkali metal alkyl sulfate, a pharmaceutically acceptable edetate, at least one alkali metal salicylate, and at least one micelle-forming compound. Generally, oral (including buccal), transdermal and nasal are the preferred sites of administration but the composition can also be applied to the rectal and vaginal mucosae.

Methods for making and using the present pharmaceutical compositions are also within the scope of the present invention.

It is therefore an aspect of the present invention to provide a pharmaceutical composition comprising a macromolecular pharmaceutical agent, an alkali metal alkyl sulfate, a pharmaceutically acceptable edetate, an alkali metal salicylate, and at least one additional micelle-forming compound.

It is a further aspect of the invention to provide such a composition wherein the macromolecular pharmaceutical agent is in micellar form.

It is a further aspect of the invention to provide an improved method for administering macromolecular pharmaceutical agents, particularly to the oral and nasal regions of a patient.

A further aspect of the invention is to provide methods for making pharmaceutical compositions comprising macromolecular pharmaceutical agents and micelle forming compounds.

These and other aspects of the invention will be apparent from the following disclosure and appended claims.

DETAILED DESCRIPTION OF THE INVENTION

The present invention is directed to a pharmaceutical composition comprising: an effective amount of a macromolecular pharmaceutical agent; an alkali metal alkyl sulfate; a pharmaceutically acceptable edetate; at least one alkali metal salicylate; at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, and a suitable solvent. The alkali metal alkyl sulfate, the edetate, and the alkali metal salicylate are each present in a concentration between about 1 and 20 wt./wt. % of the total composition, each micelle-forming compound concentration is between about 1 and 20 wt./wt. % of the total composition, and the total concentration of the alkali metal alkyl sulfate, edetate, alkali metal salicylate and the micelle-forming compound together is less than 50 wt./wt. % of the total composition.

As used herein, the term "macromolecular", when used in conjunction with the term pharmaceutical agent, refers to pharmaceutical agents having a molecular weight greater than about 1000 daltons; preferably the macromolecular pharmaceutical agents of the present invention have a molecular weight between about 1000 and 2,000,000 daltons although even larger molecules are also contemplated.

The term "pharmaceutical agent" as used herein covers a wide spectrum of agents, and can include agents used for both human and veterinary applications including but not limited to treatment and study. The term broadly includes proteins, peptides, hormones, vaccines and drugs.

Preferred pharmaceutical agents include insulin, heparin, low molecular weight heparin (molecular weight less than about 5,000 daltons), hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides (GLP-1), large molecular antibiotics, (>2000 daltons) protein based thrombolytic compounds, platelet inhibitors, DNA, RNA, gene therapeutics, antisense oligonucleotides, opioids, narcotics, hypnotics, steroids and pain killers.

Hormones which may be included in the present compositions include but are not limited to thyroids, androgens, estrogens, prostaglandins, somatotropins, gonadotropins, erythropoetin, interferons, steroids and cytokines. Cytokines are small proteins with the properties of locally acting hormones and as used herein include, but are not limited to, various forms of interleukin (IL), and growth factors including various forms of transforming growth factor (TGP), fibroblast growth factor (FGF) and insulin-like growth factor (IGF). Vaccines which may be used in the compositions according to the present invention include bacterial and viral vaccines such as vaccines for hepatitis, influenza, tuberculosis, canary pox, chicken pox, measles, mumps, rubella, pneumonia, BCG, HIV and AIDS; bacterial toxoids include but are not limited to diphtheria, tetanus, Pseudomonas sp. and *Mycobacterium tuberculosis*. Examples of drugs, more specifically cardiovascular or thrombolytic agents, include heparin, hirugen, hirulos and hirudine. Macromolecular pharmaceutical agents included in the present invention further include monoclonal antibodies, polyclonal antibodies and immunoglobins. This list is not intended to be exhaustive.

A preferred macromolecular pharmaceutical agent according to the present invention is insulin. "Insulin" as used herein encompasses naturally extracted human insulin, or competently produced human insulin, insulin extracted from bovine, porcine or other mammalian sources, recombinantly produced human, bovine, porcine or other mammalian insulin, insulin analogues, insulin derivatives, and mixtures of any of these insulin products. The term further encompasses the insulin polypeptide in either its substantially purified form, or in its commercially available form in which additional excipients are added. Various forms of insulin are commercially available. An "insulin analogue", as that term is used herein, encompasses any of the insulins defined above wherein one or more of the amino acids within the polypeptide chain has been replaced with an alternative amino acid, wherein one or more of the amino acids have been deleted, or wherein one or more amino acids is added. "Derivatives" of insulin refers to insulin or analogues thereof wherein at least one organic substituent is bound to one or more of the amino acids in the insulin chain.

The macromolecular pharmaceutical agent exists in micellar form in the present pharmaceutical compositions. As will be appreciated by those skilled in the art, a micelle is a colloidal aggregate of amphipathic molecules in which the polar hydrophilic portion of the molecules extends outwardly while the non-polar hydrophobic portion extends inwardly. The micelle encapsulates the molecule of interest. As discussed below, various combinations of micelle-forming compounds are utilized in order to achieve the present formulation. It is believed that the presence of the micelles significantly aids in the absorption of the macromolecular pharmaceutical agent both because of their enhanced absorption ability, and also because of their size. In addition, encapsulating pharmaceutical agents in micelles protects the agents from rapid degradation in the GI environment.

The particle size of the micelles will typically be in the range of 1 to 10 nanometers. Preferably, the micelle size ranges between 1 and 5 nanometers.

An effective amount of the macromolecular pharmaceutical agent should be included in the present composition. As used herein, the term "effective amount" refers to that amount of the pharmaceutical agent needed to bring about the desired result, such as obtaining the intended treatment or prevention of a disorder in a patient, or regulating a physiological condition in a patient. As used herein, the term "patient" refers to members of the animal kingdom, including but not limited to humans. It will be appreciated that the effective amount will vary depending on the particular agent used, the parameters determined for the agent, the nature and severity of the disorder being treated, the patient being treated, and the route of administration such as nasal, oral, rectal or vaginal. The determination of what constitutes an effective amount is well within the skill of one practicing in the art. In the case of insulin, the effective amount will typically be between about 1 to 20 wt./wt. % of the total composition.

Any alkali metal alkyl sulfate can be used in the present compositions, provided compatibility problems do not arise. Preferably, the alkyl is a C8 to C22 alkyl, more preferably lauryl (C12). Any alkali metal can be utilized, with sodium being preferred. While the alkali metal alkyl sulfate is generally present in a concentration of between 1 and 20 wt./wt. % of the total composition, a concentration of from 2 to 5 wt./wt. % of the total composition is preferred.

As used herein, the term "edetate" refers to pharmaceutically acceptable salts of ethylenediaminetetraaceticacid. Preferably, the edetate is an alkali metal edetate, more preferably disodium edetate or dipotassium edetate, or combinations thereof. The edetate is present in a concentration from about 1 to 20 wt./wt. %

The alkali metal salicylate of the composition is, preferably, sodium salicylate. The alkali metal salicylate is present in a concentration from about 1 to 20 wt./wt. %.

In one embodiment the alkali metal alkyl sulfate, edetate and alkali metal salicylate are each present in a concentration of from 2 to 5 wt./wt. % of the total composition.

The compositions of the present invention further comprise at least one micelle-forming compound selected from the group comprising lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof. Each micelle-forming compound listed above is present in the composition in a concentration of between about 1 and 20 wt./wt. % of the total composition. More preferably, each micelle-forming compound is present in a concentration of between about 1 and 5 wt./wt. % of the total composition. The alkali metal alkyl sulfate functions as a micelle forming agent, and is added to the composition in addition to the one or more other micelle-forming compounds listed herein. The total concentration of alkali metal alkyl sulfate, the alkali metal salicylate, the edetate and the micelle-forming compounds together is less than 50 wt./wt. % of the total composition.

The alkali metal alkyl sulfate functions as a micelle-forming agent, and is added to the composition in addition to the one or more other micelle-forming compounds listed herein. The total concentration of the alkali metal alkyl sulfate, alkali metal salicylate, edetate and the one or more micelle-forming compound together is less than 50 wt./wt. % of the composition.

It will be appreciated that several of the micelle-forming compounds are generally described as fatty acids, bile acids, or salts thereof. The best micelle-forming compounds to use may vary depending on the pharmaceutical agent used and can be readily determined by one skilled in the art. In general, bile salts are especially suitable for use with hydrophilic drugs and fatty acid salts are especially suitable for use with lipophilic drugs. Because the present invention uses relatively low concentrations of bile salts, toxicity problems associated with use of these salts is minimized, if not avoided.

The lecithin can be saturated or unsaturated, and is preferably selected from the group consisting of phosphatidylcholine, phosphatidylserine, sphingomyelin, phosphatidylethanolamine, cephalin, and lysolecithin and mixtures thereof. Saturated and unsaturated lecithin are commercially available from The American Lecithin Co. as Phospholipon-H™0 and Phospholipon-G™, respectively.

Preferred salts of hyaluronic acid are alkali metal hyaluronates, especially sodium hyaluronate, alkaline earth hyaluronates, and aluminum hyaluronate. When using hyaluronic acid or pharmaceutically acceptable salts thereof in the present compositions, a concentration of between about 1 and 5 wt./wt. % of the total composition is preferred, more preferably between about 1.5 and 3.5 wt./wt. %.

In preferred embodiments of the present invention, at least two micelle-forming compounds are used. The micelle-forming compound combination is selected from the group consisting of i) sodium hyaluronate and saturated phospholipid, ii) lecithin and sodium hyaluronate, iii) sodium hyaluronate and evening of primrose oil, iv) saturated phospholipid and glycolic acid, v) saturated phospholipid, glycolic acid and lactic acid, vi) sodium hyaluronate, oleic acid and gamma linoleic acid, and vii) trihydroxy oxocholanyl glycine, lecithin and chenodeoxycholate.

The above-described components of the present composition are contained in a suitable solvent. The term "suitable solvent" is used herein to refer to any solvent in which the components of the present invention can be solubilized, in which compatibility problems do not arise, and which can be administered to a patient. Any suitable aqueous or nonaqueous solvent can be used. A particularly preferred solvent is water. Other suitable solvents include alcohol solutions, especially ethanol. Alcohol should be used at concentrations that will avoid precipitation of the components of the present compositions. Enough of the solvent should be added so that the total of all the components in the composition is 100 wt./wt. %, i e. solvent to q.s. Typically, some portion of the solvent will be used initially to solubolize the pharmaceutical agent prior to addition of the micelle-forming compounds. The composition will typically contain between about 1 to 20 wt./wt. % of the solvent, depending on the desired dilution and dosage needed.

The present compositions optionally contain a stabilizer and/or a preservative. Phenolic compounds are particularly suited for this purpose as they both stabilize the composition and protect against bacterial growth. A phenolic compound will be understood as referring to a compound having one or more hydroxy groups attached directly to a benzene ring. Preferred phenolic compounds according to the present invention include phenol and methyl phenol (also known as m-cresol), and mixtures thereof.

The compositions of the present invention can further comprise one or more of the following: inorganic salts; antioxidants; protease inhibitors; and isotonic agents. The amount of any of these optional ingredients to use in the present compositions can be determined by one skilled in the art. It will be understood by those skilled in the art that colorants, flavoring agents and non-therapeutic amounts of other compounds may also be included in the formulation. Typical flavoring agents are menthol, sorbitol and fruit flavours. When menthol is used as one of the micelle-forming compounds, therefore, it will also import flavor to the composition.

For example, some compositions, including those which contain insulin, may also contain at least one inorganic salt; the salt should be one which opens channels in the GI tract and which may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. The antioxidant can be selected from the group consisting of tocopherol, deteroxime mesylate, methyl paraben, ethyl paraben, ascorbic acid and mixtures thereof, as well as other antioxidants known in the pharmaceutical arts. A preferred antioxidant is tocopherol. The parabens will also provide preservation to the composition.

Protease inhibitors serve to inhibit degradation of the pharmaceutical agent by the action of proteolytic enzymes. When used, protease inhibitors are preferably in a concentration of between about 1 and 3 wt./wt. % of the composition. Any material that can inhibit proteolytic activity can be used, absent compatibility problems. Examples include but are not limited to bacitracin and bacitracin derivatives such as bacitracin methylene disalicylates, soybean trypsin, and aprotinin. Bacitracin and its derivatives are preferably used in a concentration of between 1.5 and 2 wt./wt. % of the total composition, while soyabean trypsin and aprotinin are preferably used in a concentration of between about 1 and 2 wt./wt. % of the total composition.

An isotonic agent such as glycerin or dibasic phosphate may also be added after formation of the mixed micellar composition. The isotonic agent serves to keep the micelles in solution. When glycerin is used as one of the micelle-forming compounds it will also function as an isotonic agent. When dibasic sodium phosphate is used it will also serve to inhibit bacterial growth.

The pH of the present pharmaceutical composition should typically be in the range of 5 to 8, more preferably 6 to 7. Hydrochloric acid or sodium hydroxide can be utilized to adjust the pH of the composition as needed.

The compositions of the present invention may be stored at room temperature or at cold temperature. Storage of proteinic drugs is preferable at a cold temperature to prevent degradation of the drugs and to extend their shelf life.

The present invention, therefore, provides a pharmaceutical composition in which a macromolecular pharmaceutical agent is encapsulated in mixed micelles formed by a combination of micelle-forming agents. The composition is preferably delivered through the oral, nasal, rectal or vaginal cavities, with buccal delivery being more preferred. Both the oral and nasal membranes offer delivery advantages, in that drugs administered through these membranes have a rapid onset of action, provide therapeutic plasma levels, avoid the first pass effect of hepatic metabolism, and avoid exposure of the drug to the hostile GI environment. An additional advantage is the easy access to membrane sites, so that the drug can be applied, localized and removed easily. Prolonged delivery of large molecules may be achieved through these membranes.

Oral routes of administration may be particularly advantageous. The sublingual mucosa includes the membrane of the ventral surface of the tongue and the floor of the mouth, and the buccal mucosa is the lining of the cheeks. The sublingual mucosa is relatively permeable, allowing for the rapid absorption and acceptable bioavailability of many drugs. Further, the buccal mucosa is convenient and easily accessible. In comparison to the GI tract and other organs, the buccal environment has a neutral pH, therefore allowing for a longer effective life of the drug in vivo. The sublingual mucosa and buccal mucosa are collectively referred to herein as the "oral mucosae".

It is believed that improvements in penetration and absorption of the present mixed micellar formulations can be achieved by administering the present compositions with propellants such as tetrafluoroethane, heptafluoroethane, dimethylfluoropropane, tetrafluoropropane, butane, isobutane, dimethyl ether and other non-CFC and CFC propellants. Preferably, the ratio of pharmaceutical agent to propellant is from 5:95 to 25:75. The preferred propellants are hydrogen-containing chlorofluorocarbons, hydrogen-containing fluorocarbons, dimethyl ether and diethyl ether. Even more preferred is HFA-134a (1,1,1,2-tetrafluoroethane).

Preferably, the present compositions are delivered through metered dose spray devices. Metered dose inhalers are known and are a popular pulmonary drug delivery form for some drugs. One benefit of using a metered dose device is the ability to deliver a precise amount of medication with each application, and another is that the potential for contamination is minimized because the devices are self-contained.

The present invention also provides a process for making the pharmaceutical composition of the present invention. The present compositions may be prepared by mixing a solution of the macromolecular pharmaceutical agent, the alkali metal alkyl sulfate, the alkali metal salicylate, the edetate, at least one micelle-forming compound, and optionally the stabilizer and other additives. The pharmaceutical agent should be added in an amount effective for the desired purpose. Mixed micelles will form with substantially any kind of mixing of the ingredients but vigorous mixing is preferred in order to provide smaller size micelles. The pharmaceutical agents, solvents, alkali metal alkyl sulfates, alkali metal salicylate, pharmaceutically acceptable edetate, micelle-forming compound(s) and optional additives as described above for the present compositions are all suitable for use in the present processes.

In one method a first micellar composition is prepared which contains the pharmaceutically active agent and at least the alkali metal alkyl sulfate, the edetate and the alkali metal salicylate to form a first micellar composition. The first micellar composition is then mixed with at least one additional micelle-forming compound to form a mixed micellar composition. In another method, there is an additional step of adding an additional micelle-forming compound different from the first. Preferably, the first micelle-forming compound is lecithin.

The stabilizer, preferably phenol and/or m-cresol, may be added during or after the addition of the micelle-forming compound to the mixed micellar composition to stabilize the formulation and protect against bacterial growth. An isotonic agent may also be added after formation of the mixed micellar composition, as can any of the other optional additives as described above. The formulation can then be put into an aerosol dispenser and the dispenser charged with the propellant, if administration by this route is desired. The propellant, which is under pressure, is in liquid form in the dispenser. When the composition of the present invention is in a dispenser, the aqueous phase may be separated from the propellant phase. Preferably, however, the ratios of the ingredients are adjusted by simple experimentation so that the aqueous and propellant phases become one, i.e., there is one phase. If there are two phases, it is necessary to shake the dispenser prior to dispensing a portion of the contents, such as through a metered valve. The dispensed dose of pharmaceutical agent is propelled from the metered valve in a fine spray.

One embodiment of the present processes provides for making the present pharmaceutical compositions by:
a) mixing a macromolecular pharmaceutical agent in a suitable solvent with an alkali metal alkyl sulfate, an edetate and an alkali metal salicylate; and
b) subsequently adding at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, to form a micellar macromolecular pharmaceutical agent composition.

Each of the micelle-forming compounds (if more than one is used), the alkali metal alkyl sulfate, the edetate and the alkali metal salicylate is present in a concentration of from 1 to 20 wt./wt. % of the total composition, with the total being less than 50 wt./wt. % of the total composition.

The method can, optionally, further comprise the step of adding a phenolic compound selected from the group consisting of phenol, m-cresol and mixtures thereof after the addition of the micelle-forming compounds.

The method can further comprise the step of placing the composition into an aerosol dispenser and charging the dispenser with a propellant.

In another embodiment, the process comprises:
a) mixing a macromolecular pharmaceutical agent in a suitable solvent with an alkali metal alkyl sulfate, an edetate, and an alkali metal salicylate;
b) subsequently adding at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, to form a micellar macromolecular pharmaceutical agent composition; and
c) after step b), adding at least one additional micelle-forming compound which is different from that added in step b) but selected from the same group. Preferably, the micelle-forming compound selected in step b) is lecithin.

Again, during or after step b), a phenolic compound as described above can be added to the composition. Mixing can be vigorous or not. Vigorous mixing may be accomplished by using high-speed stirrers, such as magnetic stirrers, propeller stirrers, or sonicators, and is preferred.

The present invention also provides a metered dose aerosol dispenser with the composition of the present invention and a propellant contained therein, in which a solution containing the macromolecular pharmaceutical agent and the propellant are in a single phase.

The present invention also provides a method for administering the pharmaceutical compositions of the present invention, by spraying the intermixed composition into the mouth with a metered dose spray device. Application can be to the buccal cavity by spraying into the cavity, without inhalation. It may be necessary or desirable to shake the dispenser prior to spraying the present pharmaceutical composition and propellant into the buccal cavity. The plasma levels and blood glucose levels when orally administering the present insulin-containing compositions are comparable to those achieved when insulin is injected; the present methods offer significant improvements in the quality of life over injection including pain-free and needle-free therapy and improved convenience.

In the case of insulin, which is intended for administration through the oral cavity, a first micellar solution may be made by adding a buffer solution to powdered insulin, and stirring until the powder is dissolved and a clear solution is obtained. A typical buffer solution is sodium salicylate, disodium edetate, and sodium lauryl sulfate. A typical concentration of sodium lauryl sulfate, sodium salicylate and edetate in the aqueous solution is about 3 to 20 wt./wt. % of each compound in the solution. Typically, insulin is present in the micellar solution in an amount which will give a concentration of about 1 to 20 wt./wt. % of the final formulation depending on desired dosage.

The solution so formed may then be mixed vigorously, such as by sonication or high speed stirring, to form a micelle solution. This first micellar solution is then added slowly to the first absorption enhancing compound, e.g., lecithin, while vigorous mixing is continued. At least one other absorption enhancing compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof, and mixtures or combinations thereof is then added. The mixing may be done with a high-speed mixer or sonicator to ensure uniform micelle particle size distribution within the formulation.

In a preferred embodiment, after forming the present micellar pharmaceutical compositions, the phenol and/or m-cresol is added. As indicated above, other ingredients, such as isotonic agents, flavoring agents, anti-oxidants, salts, protease inhibitors or other pharmaceutically acceptable compounds may also be added. The composition is then charged to an aerosol dispenser and the dispenser is charged with propellant in a known manner.

The specific concentrations of the above ingredients can be determined by one skilled in the art based on the general guidelines provided herein. It will be understood that the amounts of certain ingredients may need to be limited in order to avoid compositions which produce foam when sprayed rather than forming a fine spray. For absorption through the oral cavities, it is often desirable to increase, such as by doubling or tripling, the dosage of pharmaceutical agent which is normally required through injection or administration through the gastrointestinal tract.

The desired size of aerosol droplets which are sprayed from the aerosol dispenser will depend, in part, on where the pharmaceutical is to be deposited. For example, for deposition in the lungs, particle sizes of less than about 5 $\mu$m are preferred, whereas for absorption in the buccal cavity of the mouth, particle sizes of about 5–10 $\mu$m are preferred. As mentioned previously, use of atomizers or aerosol spray devices can further reduce particle size.

For oral and nasal application, sprays are preferable, but drops, chewable tablets and gum and other suitable forms may also be used. Suitable ingredients for a chewable form include guar gum, powdered acacia, carrageenin, beeswax and xanthan gum. It is also possible to use a drug delivery system in which an enteric coating is applied to a gelatin capsule containing the micelles, so that the micelles are released in the duodenum or large intestine.

The present invention is also directed to a method for enhancing the rate of absorption of a macromolecular pharmaceutical agent comprising administering a composition comprising said agent in conjunction with an alkali metal alkyl sulfate, an edetate, an alkali metal salicylate and at least one of the micelle-forming compounds described above. Preferably, this method is carried out by administering directly to the buccal region of the patient.

Administration of the formulation into the buccal cavity, according to any of the present methods, is by spraying the formulation into the mouth, without inhalation, so that the droplets stay in the mouth rather than being drawn into the lungs.

EXAMPLES

The following examples are intended to illustrate the invention, and should not be considered as limiting the invention in any way.

Example 1

Mixed micellar oral insulin (50 units) was formulated using alkali metal lauryl sulfate and sodium salicylate (both 4.4% by wt.) and alkali metal edetate (2.2% by wt.) with Phospholipon-H™ (10 mg) and tested on healthy volunteers.

The method involved mixing the sodium lauryl sulfate, sodium salicylate and alkali metal edetate with 10 mL water in a beaker with a magnetic stirrer at medium speed until the ingredients were dissolved, to form a buffer solution. Insulin powder was placed in a beaker and to this powder was added the buffer solution. The solution was continuously stirred using a magnetic stir bar until all of the insulin powder was dissolved and a clear solution obtained. The micellar solution so formed was stored in clean glass bottles and refrigerated.

Mixed micellar insulin was then prepared in a glass beaker, in which was placed the Phospholipon-H™ and a small amount of isopropyl alcohol. The mixture was stirred at a high speed (100 rpm) for about 10 minutes to ensure complete dissolution of the Phospholipon-H™. To this solution was added the micellar insulin solution very slowly, drop wise, using a glass dropper, with continuous stirring at a high speed. The solution was stirred continuously for another 30 minutes at a high speed to ensure uniform micellar particle size distribution.

Samples of the mixed micellar solution were taken orally by the volunteers.

Blood glucose levels were monitored every 15 minutes using Bayer's glucometer Elite for 3 hours and the average results for 5 volunteers are shown in Table I.

TABLE I

| Time*: | 0 | 15 | 30 | 45 | 60 | 90 | 120 | 150 | 180 |
|---|---|---|---|---|---|---|---|---|---|
| Avg: | 6.5 | 6.1 | 5.5 | 5.3 | 5.3 | 5.4 | 5.5 | 5.5 | 5.5 |

*time in minutes

This data shows that orally administered insulin with alkali metal lauryl sulfate combined with the sodium salicylate and alkali metal edetate with Phospholipon-H™ has a small metabolic effect on blood glucose levels in healthy volunteers

Example 2

Oral insulin (50 units) was formulated using alkali metal lauryl sulfate and sodium salicylate (both 4.4% by wt.) and alkali metal edetate (2.2% by wt.) with Phospholipon_H™ (10 mg) and sodium hyaluronate (1.1% by wt). This formulation was tested on healthy subjects under fasting condition.

The method involved mixing the sodium lauryl sulfate, sodium salicylate and alkali metal edetate with water in a beaker with a magnetic stirrer at medium speed until the ingredients were dissolved, to form buffer solution. Insulin powder was placed in a beaker and to this powder was added the buffer solution. The solution was continuously stirred using a magnetic stir bar until all of the insulin powder was dissolved and a clear solution obtained. The micellar solution so formed was stored in clean glass bottles and refrigerated.

Mixed micellar insulin was then prepared in a glass beaker, in which was placed the Phospholipon-H™ and a small amount of isopropyl alcohol. The mixture was stirred at a high speed (1000 rpm) for about 10 minutes to ensure complete dissolution of the Phospholipon-H. To this solution was added the micellar insulin solution very slowly, drop wise, using a glass dropper, with continuous stirring at a high speed. The solution was stirred continuously for another 30 minutes at a high speed to ensure uniform micellar particle size distribution. The hyaluronate and small amounts of menthol and sorbitol were then added, with continuous stirring.

Samples of the mixed micellar solution were taken orally by the volunteers.

Blood glucose levels were monitored every 15 minutes using Bayer's glucometer Elite for 3 hours and the average results for 5 volunteers are shown in Table II.

TABLE II

| Time*: | 0 | 15 | 30 | 45 | 60 | 90 | 120 | 150 | 180 |
|---|---|---|---|---|---|---|---|---|---|
| Avg: | 6.5 | 5.9 | 5.6 | 5.4 | 4.9 | 5.0 | 4.9 | 5.2 | 5.4 |

*time in minutes

This data shows that orally administered insulin with alkali metal lauryl sulfate, sodium salicylate, alkali metal edetate, Phospholipon-H™ and sodium hyaluronate has resulted in lowering of blood glucose levels in healthy subjects better than the above mentioned formulations.

Example 3

A buffer solution was prepared using 0.5 g sodium lauryl sulfate, 0.5 g sodium salicylate and 0.25 g disodium edetate dissolved in 10 mL of water. The solution was added to 16 mg (400 units) of insulin and mixed, to form micellar insulin.

Separately, 100 mg of powdered Phosphatidylcholine-H was added to a glass beaker and to this powder was added 10 mL 50% ethanol. The powder was dissolved completely. This solution was then added to the above buffer solution, to give a 30 units/mg insulin solution, with vigorous mixing to form a mixed micellar solution. To this was added 0.6 mL of sodium hyaluronate and 0.2 mL of 2% menthol solution containing 3% sorbitol.

In one set of tests, ten Type II diabetic human volunteers who took insulin, by injection three times a day, were studied. In another set of tests the volunteers were tested with insulin, taken orally. The volunteers fasted from midnight prior to the test, with no food being taken during the 4-hour study.

On the first day, the volunteers received 10 units insulin by injection (regular fast acting insulin, available from Eli Lilly). On the second day, the volunteers received 30 units (1 mL volume per drop, approximately 20 drops) of the above-prepared oral insulin (3 times the injection dose). In both tests, blood glucose levels were monitored every 15 minutes by Bayer's Glucometer Elite.

The results, showing the average for the ten volunteers, were as shown on the following page:

TABLE III

| | Blood glucose levels (mmol/L) | |
|---|---|---|
| Time (minutes) | Oral Dose (30 units) | Injection (10 units) |
| 0 | 6.4 | 6.8 |
| 15 | 5.8 | 6.9 |
| 30 | 5.4 | 6.1 |
| 45 | 5.3 | 5.8 |
| 60 | 5.3 | 5.8 |
| 75 | 5.2 | 5.8 |
| 90 | 5.2 | 5.4 |
| 105 | 5.2 | 5.4 |
| 120 | 5.1 | 5.2 |
| 135 | 5.1 | 5.1 |
| 150 | 5.2 | 4.9 |
| 165 | 5.3 | 4.9 |
| 180 | 5.3 | 4.8 |
| 195 | 5.4 | 4.8 |
| 210 | 5.4 | 5.2 |
| 225 | 5.6 | 5.2 |
| 240 | 5.6 | 5.4 |

The results show that the oral insulin formulation of the present invention, at a dosage of three times higher than the injected level, is comparable to the injected insulin.

Example 4

In a 250 mL capacity glass beaker was added 5 g sodium lauryl sulfate, 5 g sodium salicylate and 2.5 g edetate. The beaker was placed on a hot plate with a magnetic stirrer. To this dry powder mixture was added 100 mL distilled water and the mixture was stirred, using the magnetic stir bar, at a medium speed until all the powder was dissolved. This buffer solution was stored in a clean glass bottle at room temperature (pH 6.5).

A micellar insulin solution was then prepared in a 50 mL capacity glass beaker, into which was placed 11.54 mg insulin powder. To this powder was added 10 mL of the buffer solution. The solution was continuously stirred using a magnetic stir bar until all of the insulin powder was dissolved and a clear solution obtained. The micellar solution so formed was stored in clean glass bottles and refrigerated.

A 2% menthol solution was then prepared from 100 mg menthol crystals, dissolved in S mL ethanol. To this solution was added 5 mg FD &C blue dye. The solution was stirred for 10 minutes and stored in a glass bottle at room temperature.

Mixed micellar insulin was then prepared in a 50 mL glass beaker, in which was placed 100 mg of phosphatidylcholine (Sigma, type I=EH, hydrogenated). To this powder was added 10 mL of isopropyl alcohol. The mixture was stirred at a high speed (1000 rpm) for about 10 minutes to ensure complete dissolution of the phosphatidylcholine. To this solution was added the micellar insulin solution very slowly, drop wise, using a glass dropper, with continuous stirring at a high speed. The solution was stirred continuously for another 30 minutes at a high speed to ensure uniform micellar particle size distribution. To this solution was added 1 mL of the 2% menthol solution and 50 mg sodium hyaluronate. The semi-clear, translucent, light blue color, insulin mixed micellar solution (final volume 15 mL) was stored in a clean glass bottle and refrigerated. The solution had a pH of 6.5.

Heating up to about 45° C. may be required, for example, using a water bath, to completely dissolve the phosphatidylcholine powder.

The micellar insulin composition should be added slowly, to ensure formation of the mixed micellar formulation.

Example 5

The formulation of Example 4 was tested in a manner similar to that indicated in Example 3 except that the formulation of the present invention was administered nasally.

On the first day, the ten volunteers each received 10 units insulin by injection (regular fast acting, Eli Lilly). On the second day, the volunteers received 20 units of the "oral" insulin of Example 4 (2 times the injected dose). The "oral" insulin was administered as drops (0.4 mL volume per drop, approximately 4 large drops in total, i.e. two drops in each nostril).

The results, showing the average for the ten volunteers, were as follows:

TABLE IV

Blood glucose levels (mmol/L)

| Time (minutes) | Nasal Dose (20 units) | Injection (10 units) |
|---|---|---|
| 0 | 7.4 | 6.8 |
| 15 | 6.7 | 7.0 |
| 30 | 5.9 | 6.8 |
| 45 | 5.3 | 6.3 |
| 60 | 5.0 | 6.3 |
| 75 | 5.2 | 5.8 |
| 90 | 5.1 | 5.2 |
| 105 | 5.0 | 5.0 |
| 120 | 4.6 | 5.2 |
| 135 | 4.5 | 4.2 |
| 150 | 4.3 | 4.6 |
| 165 | 4.3 | 4.0 |
| 180 | 4.8 | 4.1 |
| 195 | 5.3 | 4.3 |
| 210 | 5.4 | 4.5 |
| 225 | 5.7 | 4.7 |
| 240 | 5.6 | 5.0 |

The results show that the nasal insulin formulation of the present invention, at a dosage of twice the injected level, is comparable to the injected insulin.

Example 6

The formula of Example 4 was taken and tests performed to determine the insulin action on meal glucose on healthy volunteers.

Usually, diabetic patients take an insulin injection 30 minutes prior to a meal, because injected insulin takes a long time to take effect. Injected insulin is slowly absorbed into bloodstream within 60 minutes and has a metabolic effect on meal glucose levels.

The mixed micellar formulation of Example 4 was tested in healthy volunteers under controlled conditions to determine the oral insulin effect on meal glucose when compared to injected insulin.

In one set of tests, ten healthy non-diabetic human volunteers were tested with insulin, by injection. In another set of tests the volunteers were tested with insulin, taken orally. The volunteers fasted from midnight prior to the tests, with food being taken 30 minutes after dosing. The meals were standard Sustacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared oral insulin (3 times the injection dose). In both tests, blood glucose levels were monitored every 15 minutes by Bayer's Glucometer Elite. The results are shown below:

TABLE V

Blood glucose levels (mmol/L)

| Time (minutes) | Oral Dose (30 units) | Injection (10 units) |
|---|---|---|
| 0 | 5.7 | 5.5 |
| 15 | 5.2 | 5.6 |
| 30 | 5.0 | 5.4 |
| 45 | 5.3 | 5.4 |
| 60 | 5.4 | 5.6 |
| 75 | 6.3 | 6.6 |
| 90 | 6.9 | 7.0 |
| 105 | 6.0 | 5.9 |
| 120 | 5.8 | 5.6 |
| 135 | 5.5 | 5.1 |
| 150 | 5.1 | 4.8 |
| 165 | 4.9 | 4.6 |
| 180 | 4.8 | 4.3 |

The results indicate that the oral insulin helps control meal glucose levels in healthy volunteers when compared to injected insulin.

Example 7

The mixed micellar formulation of Example 4 was tested in diabetic volunteers under controlled conditions to determine the oral insulin effect on meal glucose when compared to injected insulin.

In one set of tests, ten Type II diabetic human volunteers who took insulin by injection three times a day were studied. In another set of tests the volunteers were tested with insulin, taken orally. The volunteers fasted from midnight prior to the tests, with food being taken 30 minutes after dosing. The meals were standard Sustacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared oral insulin (3 times the injection dose). In both tests, blood glucose levels were monitored every 15 minutes by Bayer's Glucometer Elite.

The average results for the 10 volunteers were as follows:

TABLE VI

Blood glucose levels (mmol/L)

| Time (minutes) | Oral Dose (30 units) | Injection (10 units) |
|---|---|---|
| 0 | 8.8 | 8.7 |
| 15 | 8.1 | 8.8 |
| 30 | 8.0 | 8.9 |
| 45 | 8.4 | 10.1 |
| 60 | 10.2 | 11.8 |
| 75 | 11.8 | 11.8 |
| 90 | 12.3 | 12.2 |
| 105 | 10.8 | 11.2 |
| 120 | 9.6 | 10.4 |
| 135 | 8.1 | 8.4 |
| 150 | 6.9 | 7.3 |
| 165 | 6.2 | 6.5 |
| 180 | 4.8 | 4.3 |

The results indicate that oral insulin helps to control meal glucose levels in diabetic patients when compared to injected insulin.

Example 8

A chewable gum insulin formulation was prepared by vigorously stirring the solution of Example 4 while adding guar gum, beeswax, powdered acacia, oleic acid, gamma-linoleic acid and sorbitol. For each 30 units of insulin, the mixture contained 100 mg guar gum, 50 mg beeswax, 50 mg powdered acacia, 100 mg oleic acid, 100 mg gamma-linoleic acid and 1 mL 3% sorbitol in ethanol solution. The mixture was then poured into a flat tray coated with polytetrafluoroethylene until the mixture was about 10 mm deep. The mixture then solidified and after solidification was cut into sticks about 1 cm by 3 cm. Each stick contained about 30 units insulin.

The mixed micellar formulation in chewable stick form was tested in diabetic volunteers under controlled conditions to determine the oral insulin effect on meal glucose when compared to injected insulin.

In one set of tests, five Type II diabetic human volunteers who took insulin, by injection three times a day, were studied. In another set of tests the volunteers were tested with the chewable gum insulin, taken orally. The volunteers fasted from midnight prior to the tests, with food being taken 30 minutes after dosing. The meals were standard Sustacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared chewable gum oral insulin (3 times the injected dose). In both tests, blood glucose levels were monitored every 15 minutes by Bayer's Glucometer Elite.

The average results for the five volunteers were as follows:

TABLE VII

Blood glucose levels (mmol/L)

| Time (minutes) | Oral Dose (30 units) | Injection (10 units) |
|---|---|---|
| 0 | 9.1 | 8.8 |
| 15 | 9.3 | 8.2 |
| 30 | 9.3 | 8.0 |
| 45 | 10.2 | 8.4 |
| 60 | 11.2 | 9.2 |
| 75 | 12.1 | 10.3 |
| 90 | 12.9 | 11.8 |
| 105 | 13.2 | 11.6 |
| 120 | 12.8 | 11.0 |
| 135 | 12.2 | 10.2 |
| 150 | 11.6 | 9.6 |
| 165 | 11.0 | 9.5 |
| 180 | 10.6 | 9.1 |
| 195 | 10.0 | 8.7 |
| 210 | 9.5 | 8.2 |
| 225 | 8.8 | 8.0 |
| 240 | 8.2 | 7.5 |

Example 9

A buffer solution was prepared using 0.5 g sodium lauryl sulfate, 0.5 g sodium salicylate and 0.25 g disodium edetate dissolved in 10 mL of water. The solution was added to 8 mg (200 units) insulin and mixed, to form micellar insulin.

To this micellar solution was added 0.2 g bacitracin and 0.5 g evening of primrose oil and the solution was mixed vigorously to form a mixed micellar insulin solution (about 20 units/mL).

Six human volunteers were studied. The volunteers fasted from midnight prior to the test, with no food being taken during the 4-hour study.

On the first day, the volunteers received 10 units insulin by injection (regular fast acting insulin, available from Eli Lilly). On the second day, the volunteers received 20 units of the above-prepared oral insulin (twice the injected dose). In both tests, blood glucose levels were monitored at intervals by Bayer's Glucometer Elite.

The results, showing the average of the six volunteers, were as follows:

TABLE VIII

Blood glucose levels (mmol/L)

| Time (minutes) | Oral Dose (20 units) | Injection (10 units) |
|---|---|---|
| 0 | 8.8 | 7.9 |
| 15 | 8.4 | 7.9 |
| 30 | 8.1 | 8.2 |
| 45 | 7.4 | 8.3 |
| 60 | 6.3 | 7.6 |
| 90 | 5.1 | 6.2 |
| 120 | 5.0 | 5.2 |
| 150 | 4.8 | 4.6 |
| 180 | 5.1 | 3.9 |
| 210 | 5.3 | 4.4 |
| 240 | 5.6 | 5.2 |

The results show that the oral insulin formulation of the present invention, at a dosage of twice the injected level, is comparable to the injected insulin.

Example 10

In a 250 mL round bottom flask was added 100 mg of saturated lecithin powder (Phospholipon-90H™) purchased from the American Lecithin Co. To this powder was added 5 mL of absolute ethanol (USP grade). The flask was then attached to a rotary evaporator equipped with the vacuum pump and nitrogen inlet for inert atmosphere condition to minimize oxidation of the lecithin. The flask was rotated at 100–150 rpm under vacuum. The solution in the flask was heated to 60° C. by means of water bath to dissolve the powder completely. After complete dissolution of the powder, heating was stopped and the rotation speed was increased to 300 rpm, under vacuum in nitrogen atmosphere until the alcohol evaporated completely, leaving a uniform film on the side of the flask. The rotation was continued for at least 30 minutes to ensure uniform coating of film on the wall and complete solvent removal. After 30 minutes the rotation was stopped and the vacuum was released.

To this flask was added micellar insulin solution which had been prepared from an aqueous solution of insulin, sodium lauryl sulfate, sodium salicylate and disodium edetate. The flask was shaken with the help of shaker plate. Shaking was continued for at least 30 minutes and then the solution was sonicated with a high frequency sonicating probe for another 60 minutes in order to form small uniform mixed micelles. The mixed micelles so obtained were analyzed by Malvern Zeta™ particle size distribution measurement equipment equipped with the laser light scattering device. The mixed micelle particle size distribution obtained by this method was between 2 and 9 nm.

To this solution was added 1 mL of 2% menthol solution and 50 mg sodium hyaluronate.

The semi-clear translucent, light blue color solution (final volume 10 mL) was stored in a clean glass bottle and refrigerated. The solution had a pH of 6.5.

Example 11

A buffer solution was prepared using 0.5 g sodium lauryl sulfate, 0.5 g sodium salicylate and 0.25 g disodium edetate dissolved in 10 mL of water. The solution was added to 8 mg (200 units) insulin and mixed, to form micellar insulin.

To this micellar solution were added 0.5 g borage oil and the solution was mixed vigorously to form a mixed micellar insulin solution (about 20 units/mL)

Whereas particular embodiments of this invention have been described above for purposes of illustration, it will be evident to those skilled in the art that numerous variations of the details of the present invention may be made without departing from the invention as defined in the appended claims.

What is claimed is:

1. A pharmaceutical composition comprising:
   an effective amount of a macromolecular pharmaceutical agent;
   an alkali metal alkyl sulfate;
   at least one alkali metal salicylate;
   a pharmaceutically acceptable edetate;
   at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof, and mixtures or combinations thereof; and
   a suitable solvent;
   wherein the alkali metal alkyl sulfate, the alkali metal salicylate, the edetate and the micelle-forming compound are each present in a concentration of between about 1 and 20 wt./wt. % of the total composition, and the total concentration of the alkali metal alkyl sulfate, the alkali metal salicylate, the edetate and micelle-forming compound together is less than 50 wt./wt. % of the composition; and
   wherein the macromolecular pharmaceutical agent is in micellar form.

2. The composition of claim 1, wherein the alkali metal alkyl sulfate is in a concentration of from 2 to 5 wt./wt. % of the total formulation.

3. The composition of claim 1, wherein the alkali metal alkyl sulfate is an alkali metal C8 to C22 alkyl sulfate.

4. The composition of claim 3, wherein the alkali metal C8 to C22 alkyl sulfate is sodium lauryl sulfate.

5. The composition of claim 1, wherein the alkali metal salicylate is sodium salicylate.

6. The composition of claim 1, wherein each micelle-forming compound is present in a concentration of between about 1 and 5 wt./wt. % of the total composition.

7. The composition of claim 1, wherein one of the micelle forming compounds is lecithin.

8. The composition of claim 7, wherein the lecithin is either saturated or unsaturated and is selected from the group consisting of phosphatidylcholine, phosphatidylserine, sphingomyelin, phosphatidylethanolamine, cephalin, and lysolecithin and mixtures thereof.

9. The composition of claim 7, further comprising an additional micelle-forming compound selected from the group consisting of hyaluronic acid, pharmaceutically acceptable salts of hyaluronic acid, and mixtures thereof, wherein the concentration of such micelle-forming compound is between about 1 and 5 wt./wt. % of the total composition.

10. The composition of claim 1, wherein said salt of hyaluronic acid is selected from the group consisting of alkali metal hyaluronates, alkaline earth hyaluronates, and aluminum hyaluronates, and the concentration of said salt is between about 1 and 5 wt./wt. % of the total composition.

11. The composition of claim 10, wherein the concentration of said salt is between about 1.5 and 3.5 wt./wt. % of said total composition.

12. The composition of claim 1, wherein at least two micelle-forming compounds are used and are selected from the group consisting of i) sodium hyaluronate and saturated phospholipid, ii) lecithin and sodium hyaluronate, iii) sodium hyaluronate and evening of primrose oil, iv) saturated phospholipid and glycolic acid, v) saturated phospholipid, glycolic acid and lactic acid, vi) sodium hyaluronate, oleic acid and gamma linoleic acid, and vii) trihydroxy oxocholanyl glycine, lecithin and chenodeoxycholate.

13. The composition of claim 1, wherein the pharmaceutical agent is selected from the group consisting of insulin, heparin, low molecular weight heparin, hirulog, hirugen, huridine, cytokines, mono and polyclonal antibodies, immunoglobins, chemotherapeutic agents, vaccines, glycoproteins, bacterial toxoids, hormones, calcitonins, glucagon like peptides, antibiotics, thrombolytic compounds, platelet inhibitors, DNA, RNA, gene therapeutics, antisense oligonucleotides, steroids and pain killers.

14. The composition of claim 1, wherein the pharmaceutical agent is insulin.

15. The composition of claim 14, wherein a first micelle-forming compound is lecithin and a second micelle-forming compound is selected from the group consisting of hyaluronic acid, pharmaceutically acceptable salts of hyaluronic acid and mixtures thereof.

16. The composition of claim 1, wherein the pH of said composition is between 5 and 8.

17. The composition of claim 1, wherein said micelle size is between about 1 and 10 nanometers.

18. The composition of claim 1, wherein said solvent is selected from the group consisting of water and ethanol.

19. The composition of claim 1 further comprising one or more of the members selected from the group consisting of a phenolic compound, an antioxidant, a protease inhibitor, and an inorganic salt.

20. The composition of claim 19 wherein said composition comprises a phenolic compound selected from the group consisting of phenol, m-cresol and mixtures thereof, in a concentration of between about 1 and 10 wt./wt. % of the total composition.

21. The composition of claim 19 wherein the antioxidant is selected from the group consisting of tocopherol, deteroxime mesylate, methyl paraben, ethyl paraben, ascorbic acid and mixtures thereof.

22. The composition of claim 19 wherein the protease inhibitor is selected from the group consisting of bacitracin, bacitracin derivatives, soybean trypsin and aprotinin.

23. The composition of claim 19 wherein the inorganic salt is selected from the group consisting of sodium, potassium, calcium and zinc salts.

24. A mixed micellar pharmaceutical composition comprising at least one alkali metal salicylate, an edetate and a macromolecular pharmaceutical agent encapsulated in micelles, said micelles formed with an alkali metal alkyl sulfate and at least one compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof.

25. A process for making a pharmaceutical composition comprising:
   a) mixing an effective amount of a macromolecular pharmaceutical agent composition in a suitable solvent with an alkali metal alkyl sulfate, an alkali metal salicylate, and an edetate; and b) slowly adding while mixing, at least one micelle-forming compound selected from the group consisting of lecithin, hyaluronic acid, octylphenoxypolyethoxyethanol, glycolic acid, lactic acid, chamomile extract, cucumber extract, ooleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof, to form a mixed micelle pharmaceutical composition;

wherein the alkali metal alkyl sulfate, alkali metal salicylate, edetate and each micelle-forming compound are each present in a concentration of between about 1 and 20 wt./wt. % of the total composition, and the total concentration of alkali metal alkyl sulfate, alkali metal salicylate, edetate and micelle-forming compound together is less than 50 wt./wt. % of the total composition.

26. The process of claim 25, wherein after the addition of the micelle-forming compound of step (b) at least one additional different micelle-forming compound is mixed with the micellar composition of step (b).

27. The process of claim 25, further comprising the step of adding one or more members of the group consisting of a phenolic compound, an antioxidant, a protease inhibitor and an inorganic salt, to the mixed micelle pharmaceutical composition.

28. The process of claim 25, wherein said mixing is effected by use of a high speed stirrer selected from the group consisting of magnetic stirrers, propeller stirrers, and sonicators.

29. The process of claim 25 wherein the micelle-forming compound is formed into a film prior to the addition of the pharmaceutical agent, alkali metal alkyl sulfate, alkali metal salicylate and edetate.

30. A method for treating a patient comprising administering to said patient the pharmaceutical composition of claim 1.

31. A method for enhancing the rate of absorption of a macromolecular pharmaceutical agent in a patient comprising administering a composition comprising said agent in conjunction with an alkali metal alkyl sulfate, at least one alkali metal salicylate, an edetate and at least one micelle-forming compound selected from the group consisting of lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogs thereof and mixtures or combinations thereof.

\* \* \* \* \*